US 6,812,354 B2
Nov. 2, 2004

(12) United States Patent
Beavers et al.

(54) PROCESS FOR PREPARING 3-METHYLTETRAHYDROFURAN

(75) Inventors: William Anthony Beavers, Longview, TX (US); Alexey Victorovitch Ignatchenko, Longview, TX (US)

(73) Assignee: Eastman Kodak Company, Kingsport, TN (US)

( * ) Notice: Subject to any disclaimer, the term of this patent is extended or adjusted under 35 U.S.C. 154(b) by 0 days.

(21) Appl. No.: 10/324,960

(22) Filed: Dec. 20, 2002

(65) Prior Publication Data

US 2004/0122241 A1 Jun. 24, 2004

(51) Int. Cl.$^7$ ............... C07D 307/00; C07D 307/02
(52) U.S. Cl. ................................. 549/429; 549/497
(58) Field of Search ............................. 549/429, 497

(56) References Cited

U.S. PATENT DOCUMENTS 4,877,909 A    10/1989   Mizusaki et al.
6,521,765 B1    2/2003   Ignatchenko et al.

FOREIGN PATENT DOCUMENTS

EP           1 057 823         12/2000

OTHER PUBLICATIONS

Takahashi et al, Bull. Chem. Soc. Japan, vol. 65, No. 1, 1992, pp. 262–266.

*Primary Examiner*—Rita Desai
*Assistant Examiner*—Raymond Covington
(74) *Attorney, Agent, or Firm*—Michael J. Blake; Bernard J. Graves, Jr.

(57) ABSTRACT

Disclosed is a process for the preparation of 3-methyltetrahydrofuran (MeTHF) from 3-(hydroxymethyl) tetrahydrofuran (HOMeTHF) or 3-formyltetrahydrofuran (FTHF) by contacting HOMeTHF or 3-formyltetrahydrofuran with a secondary alcohol in the presence of a hydrous zirconia catalyst.

17 Claims, No Drawings

PROCESS FOR PREPARING 3-METHYLTETRAHYDROFURAN

FIELD OF THE INVENTION

This invention pertains to a novel process for preparing 3-methyltetrahydrofuran (MeTHF) from 3-(hydroxymethyl) tetrahydrofuran (HOMeTHF) or 3-formyltetrahydrofuran (3-formyl-THF or FTHF). More specifically, this invention pertains to a process for converting HOMeTHF or FTHF to MeTHF by contacting HOMeTHF or FTHF with a secondary alcohol in the presence of a zirconia catalyst.

BACKGROUND OF THE INVENTION

The Meerwein-Ponndorf-Verley reaction is a mild and selective method to reduce aldehydes and ketones using a secondary alcohol as a hydrogen source. The catalyst employed usually is a monomeric secondary trialkoxy aluminum acting formally as an agent to transfer hydride from the alpha-position of the source secondary alcohol to the carbonyl carbon of the target aldehyde or ketone. Other catalysts such as magnesium alkoxides, halo magnesium alkoxides, sodium alkoxides, stannic alkoxides, and zirconium alkoxides also are effective but generally not as effective as the aluminum alkoxides. See, for example, A. L. Wilds, *Organic Reactions*, 2, 178 (1944). U.S. Pat. No. 4,783,559 disclose the use of partially dehydrated hydroxides of titanium, tin, iron, aluminum, cerium, niobium, and zirconium to catalyze this reaction acting in either the gas or liquid phase in fixed beds as heterogeneous catalysts thereby eliminating the cumbersome workup necessary with the conventional aluminum alkoxides. U.S. Pat. No. 4,810,825 describes the use of these catalysts to reduce carboxylic acids, esters, amides, and nitrites to alcohols using secondary alcohols as the hydrogen source and U.S. Pat. No. 4,847,424 discloses catalysts to reduce carboxylic acids, esters, amides, and nitrites to aldehydes using formic acid as the hydride source. These discoveries have increased the understanding and appreciation of the strength of the hydride transfer potential of these agents since reducing these functional groups normally requires very forcing conditions with special catalysts, as described in *Catalytic Hydrogenation Over Platinum Metals*, P. N. Rylander, Academic Press, Inc. Pubs, New York (1967) pages 229–237, or stoichiometric amounts of strong metal hydrides as described by W. G. Brown, *Organic Reactions*, 6, 469 (1951) and in *Reagents for Organic Synthesis*, L. F. Fieser and M. Fieser, John Wiley & Sons, Inc. Pubs., New York (1967) pages 581–595.

The selective hydrogenolysis of primary alcohols is very difficult unless the alcohol is allylic or benzylic, further suggesting a carbonium ion intermediate. Indeed, alcohols often are used as solvents for the hydrogenolysis of esters and carboxylic acids, as is disclosed in *Catalytic Hydrogenation Over Platinum Metals*, supra. One reliable method of hydrogenolyzing a primary alcohol is to convert it to an active leaving group derivative such as a tosylate, a mesylate, a halide, or a trifluoroacetate, which then is treated with a strong metal hydride in stoichiometric amounts. However, the cost of the reagents and the inefficient use of materials makes this method impractical for most industrial applications.

While there are numerous literature sources describing routes to MeTHF, most of them use multi-step approaches such as, for example, EP 0 727 422, which employs a four-step process starting with methyl methacrylate. Other processes use expensive starting materials such as citraconic anhydride derived from citric acid.

The MeTHF produced in accordance with the present invention is useful as an industrial solvent and, more importantly, as a monomer in the manufacture of polymers such as elastomers. MeTHF is used extensively as a modifier for plasticizers giving modified glass transition temperatures and broader elastic ranges.

BRIEF SUMMARY OF THE INVENTION

A process has been developed for the conversion of HOMeTHF or FTHF to MeTHF by contacting HOMeTHF or FTHF with a secondary alcohol. The process is performed in the presence of a catalyst that comprises a hydrous zirconia. The process may be run under inert atmosphere or in the presence of hydrogen or a mixture thereof.

DETAILED DESCRIPTION OF THE INVENTION

The process of the present invention provides a means for the preparation of MeTHF by contacting HOMeTHF or FTHF, or a mixture thereof, with a secondary alcohol, which serves as a hydrogen source, in the presence of a hydrous zirconia catalyst. The HOMeTHF or FTHF starting materials are commercially available or may be made by processes known to those skilled in the art. See, for example, U.S. Pat. No. 5,840,928 to Satoh et al., which describes a method for making FTHF. Further, the HOMeTHF may be obtained by contacting FTHF with hydrogen in the presence of a hydrogenation catalyst to convert FTHF to HOMeTHF. See, for example, co-pending U.S. application Ser. No. 10/125,664.

In the process of the present invention, the hydrogen source is a secondary alcohol such as 2-propanol, 2-butanol, 2-pentanol, 3-pentanol, 3-methyl-2-butanol, 2-hexanol, 3-hexanol, 3-methyl-2-pentanol, 2-methyl-3-pentanol, 1-phenyl-2-propanol, 1,3-diphenyl-2-propanol and cyclohexanol and their derivatives. The secondary alcohols preferably are secondary alkanols or cycloalkanols, i.e., saturated, aliphatic and cycloaliphatic alcohols, containing from 3 to about 20 carbon atoms. 2-Propanol (or isopropanol) and cyclohexanol are the most preferred secondary alcohols. Benzylic and allylic alcohols are not suitably because they tend to hydrogenolyze under the reaction conditions.

The amount of secondary alcohol used normally should be at least 1 mole per mole of HOMeTHF, or when FTHF is used, at least 2 moles of secondary alcohol per mole of FTHF. In addition, the secondary alcohol may be used in excess, e.g., as a process solvent, to give secondary alcohol:HOMeTHF or FTHF mole ratios as high as 1000:1. Higher ratios of secondary alcohol will speed up the reaction by the laws of mass action. Therefore, preferred ratios are 1:1 to 500:1 with ratios in the range of 5:1 to 100:1 being most preferred. Even though the process may be performed outside these limits, the inconvenience of product recovery detracts from their practical use.

The process may be run under inert atmosphere using nitrogen, argon, carbon dioxide, or other inert gases; that is, an atmosphere or gas that is non-reactive under the process conditions. Hydrogen gas can also be present, although it is not required; in fact, the process may be run in the substantial absence of an added hydrogen gas stream. Hydrogen gas, when present, may assist in the conversion of HOMeTHF or FTHF to MeTHF, as it may serve as an additional source of hydrogen for the conversion. However, the primary source of hydrogen in the present invention is a secondary alcohol.

The hydrous zirconia used in our novel process may be any of a number of commercially available zirconia catalysts, which are commonly used as support media for other metals or metal complexes. In the alternative, the hydrous zirconia catalyst for use in the present invention may be made by processes known to those of skill in the art.

For example, the hydrous zirconia catalyst may be prepared by treating a zirconium salt or other zirconium precursor compound with a base. Any of the zirconium salts serve as starting materials for the catalyst preparation, although the preferred salts are soluble in water since the preferred method of preparation uses a base precipitation. Examples of zirconium precursor compounds, which may be used include zirconium chloride, zirconium bromide, zirconium iodide, zirconium fluoride, zirconyl chloride, zirconyl bromide, zirconyl iodide, zirconyl fluoride, zirconium nitrate, zirconium sulfate, zirconium bicarbonate, zirconium carbonate, zirconium hydroxide, hydrated zirconias, and zirconium containing organometallic or inorganic complexes. A preferred zirconium source is zirconyl chloride or zirconyl nitrate owing to their availability and water solubility.

Synthesis may employ any of the usual methods known to those of skill in the art, including roasting, precipitation, or thermal decomposition. Base catalyzed precipitation is preferred because of problems maintaining the proper acidity and water content accompanying the other methods. The base used may be any of the usual base materials, or even the more exotic base materials although there is no particular advantage in the choice of exotic bases since the function of the base is to replace the zirconium counterion with hydroxide or oxide and to control the pH of the environment. Thus, lithium hydroxide, sodium hydroxide, potassium hydroxide, lithium carbonate, sodium carbonate, potassium carbonate, ammonium hydroxide, ammonium carbonate, or any organic amine containing 1 to 20 carbon atoms may be used as the base.

A preferred method for preparing the hydrous zirconia catalyst comprises dissolving the zirconium source in water prior to treatment with the base. The concentration of the water solution is not critical, with any amount from 0.01 to 95 weight percent or saturation being suitable, and concentrations of from 1 to 50 weight percent, and 10 to 20 weight percent, in water being typical. After treating the zirconium salt solution with the base to the proper pH (i.e., near neutrality; for example, about 5 to about 7), the crude hydrous zirconia is precipitated and recovered by filtration or centrifugation. The crude hydrous zirconia catalyst is washed thoroughly with, for example, water to remove as much of the original counter ion (i.e., the anion on the starting Zr salt) as possible, thereby avoiding contaminants that could modify the catalytic properties and/or performance. Thus, for example, at least 90 weight percent, preferably at least 99.9 weight percent, of the original counter-ion is removed by washing to produce an active catalyst.

The final treatment to prepare the active catalyst is calcining. Calcination is carried out at a temperature in the range of about 200°–600° C. with about 250'–500° C. being more preferred, and about 300°–400° C. being most preferred. The calcination conditions determine the residual water content and the surface area of the catalyst, which both affect the catalytic activity. The calcining time depends on the final properties desired, but ranges of 10 minutes to 100 hours are preferred with 0.5–10 hours more preferred, and 1–3 hours most preferred. The surface area of the hydrous zirconia catalyst is about 3 to about 300 $M^2$/gram, more preferably about 30 to about 150 $M^2$/gram, and most preferably about 40 to about 60 $M^2$/gram.

The amount of catalyst employed in the embodiments of the present invention can vary substantially depending on the mode of operation and other process variables. Typically, the amount of hydrous zirconia catalyst utilized in the present process should be at least an amount which gives a gram atom Zr:mole HOMeTHF or FTHF of 0.0001:1, preferably 0.01:1 to 10:1, more preferably 0.1:1 to 2:1, and most preferably about 0.01:1 to about 0.5:1. Lower catalyst:reactant ratios are more typical for autoclave/slurry modes and the higher ratios are more typical for fixed bed systems.

The process of the present invention can be carried out in the presence of an extraneous solvent, although the solvent is not required. Typically, the solvent would be inert; i.e., a solvent that is non-reactive under the process conditions. A preferred solvent is water, which helps to keep the catalyst hydrous and to reduce by-product formation. The addition of water is generally not required, however, since water is generally a co-product of the reaction of the present invention. Other solvents compatible with the high reaction temperatures may be present. Examples of such solvents include tetrahydrofuran, tetrahydropyran, toluene, xylenes, and alkanes of 5 to 20 carbons. Some or all of the solvent can also be a primary or tertiary alcohol, or a secondary alcohol, which as previously stated is the primary hydrogen source. The amount of solvent used may vary up to 99 parts by weight per part by weight of the HOMeTHF or FTHF reactant.

The process may be carried out at temperatures in the range of about 200 to about 500° C., preferably about 240 to about 400° C. and most preferably about 260 to about 350° C. Reaction pressure may be from about 1 to about 10000 psi (pounds per square inch) (or about 0.069 bar to about 689.5 bar), preferably about 200 to about 2000 psi (or about 13.79 to about 137.90 bar), and more preferably about 400 to about 800 psi (or about 27.58 to about 55.16 bar).

The reaction time required to have satisfactory results will vary significantly depending upon a number of process variables such as process temperature and pressure and the particular catalyst employed. The process preferably is operated in a manner that conversion of the HOMeTHF or FTHF reactant is maintained below 85 mole percent to maximize conversion to MeTHF product and to minimize conversion to by-products. The time range in a batch autoclave process normally is from about 0.1 to about 10 hours residence time, with about 1 to about 5 hours being more typical. In a continuous vapor phase process the residence time is usually in the range from about 1 to about 30 seconds, with about 5 to about 10 seconds being more typical.

The process can be carried as a batch autoclave process, continuous trickle bed, or vapor phase process, batch distillation, or a reactive distillation, when the catalyst is used as a packing material in the distillation column.

EXAMPLES

The processes provided by the present invention are further illustrated by the following examples. All percentages given in the examples are by weight unless specified otherwise. As used herein, the percent conversion of HOMeTHF (or FTHF) is:

$$\frac{\text{Moles } HOMeTHF \text{ (or } FTHF\text{) Converted to All Products}}{\text{Moles } HOMeTHF \text{ (or } FTHF\text{) Fed}} \times 100$$

and percent selectivity to a compound is:

$$\frac{\text{Moles } HOMeTHF \text{ (or } FTHF\text{) Converted to a Compound}}{\text{Moles } HOMeTHF \text{ (or } FTHF\text{) Converted to All Products}} \times 100$$

In the batch run examples that follow, the process was performed under a nitrogen atmosphere. The pressure at the start of the experiment was ambient, with the pressure rising during the process to about 600 to about 800 psig.

Example 1
Reduction of HOMeTHF with Secondary alcohol, Batch Run—Commercial Zirconia Catalyst A mixture of HOMeTHF (10.2 g, 0.1 mol), isopropanol (24.0 g, 0.4 mol) and commercial zirconia catalyst (Engelhard, 5.0 g; Engelhard product designation ZR-0404) was heated in an autoclave for 6 hrs at 280° C. At the end of the reaction the mixture was analyzed by GC. The selectivity to MeTHF was 59.6 percent at 36.5 percent conversion.

Example 2
Reduction of FTHF with Secondary alcohol, Batch Run—Commercial Zirconia Catalyst A mixture of FTHF (10.0 g, 0.1 mol), isopropanol (24.0 g, 0.4 mol) and commercial zirconia catalyst (Engelhard, 18.0 g) was heated in an autoclave for 3 hrs at 280° C. and for 1 hr and 330° C. At the end of the reaction the mixture was analyzed by GC. The conversion was 100 percent. The selectivity was 32.8 percent to MeTHF, 41.5 percent to HOMeTHF, and 5.5 percent to tetrahydrofuran.

Example 3
Reduction of FTHF with Secondary alcohol, Batch Run—Commercial Zirconia Catalyst A mixture of FTHF (10.0 g, 0.1 mol), isopropanol (24.0 g, 0.4 mol) and commercial zirconia catalyst (Engelhard, 18.0 g) was heated in autoclave for 6 hrs at 280° C. At the end of the reaction the mixture was analyzed by GC. The conversion was 100 percent. The selectivity was 31.7 percent to MeTHF, 48.4 percent to HOMeTHF, and 4.4 percent to tetrahydrofuran.

Example 4
Reduction of HOMeTHF with Secondary alcohol, Continuous Run—Commercial Zirconia Catalyst A mixture of HOMeTHF (102 g, 1.0 mol) and isopropanol (240 g, 4.0 mol) was fed into a one inch tubular reactor filled with commercial zirconia catalyst (100 g) at 33 ml/hr rate at 350° C. for 6 hrs. The product was collected every 60 min and analyzed by GC. The selectivity to the MeTHF was 74.7 percent at 62.5 percent conversion at the end of 6 hrs.

Example 5
Reduction HOMeTHF with Secondary alcohol, Continuous Run, Different Conditions—Commercial Zirconia Catalyst A mixture of HOMeTHF (102 g, 1.0 mol) and isopropanol (240 g, 4.0 mol) was fed into a one inch tubular reactor filled with commercial zirconia catalyst (100 g) at 33 ml/hr rate at 300° C. for 6 hrs. Nitrogen gas was co-fed at 60 ml/hr rate. The product was collected every 60 min and analyzed by GC. The selectivity to MeTHF was 59.0 percent at 17.1 percent conversion at the end of 6 hrs.

The invention has been described in detail with particular reference to preferred embodiments thereof, but it will be understood that variations and modifications can be effected within the spirit and scope of the invention.

We claim:

1. A process for preparing 3-methyltetrahydofuran (MeTHF), which comprises contacting 3-(hydroxymethyl) tetrahydrofuran (HOMeTHF) or 3-formyl-tetrahydrofuran (FTHF), or a mixture thereof, in a reaction zone with a secondary alcohol in the presence of a hydrous zirconia catalyst.

2. A process according to claim 1 wherein the contacting is conducted under an inert atmosphere.

3. A process according to claim 1 wherein the secondary alcohol is a saturated alkanol or a saturated cycloalkanol.

4. A process according to claim 3 wherein the secondary alcohol is 2-propanol, 2-butanol, 2-pentanol, 3-pentanol, 3-methyl-2-butanol, 2-hexanol, 3-hexanol, 3-methyl-2-pentanol, 2-methyl-3-pentanol, 1-phenyl-2-propanol, 1,3-diphenyl-2-propanol, cyclohexanol or a mixture thereof.

5. A process according to claim 4 wherein the secondary alcohol is 2-propanol or cyclohexanol.

6. A process according to claim 2 wherein the secondary alcohol is 2-propanol and the inert atmosphere comprises nitrogen or carbon dioxide.

7. A process according to claim 1 wherein the contacting is carried out in the presence of a solvent selected from the group consisting of water, tetrahydrofuran, tetrahydropyran, toluene, xylenes, and alkanes of 5 to 20 carbons.

8. A process according to claim 6 wherein the process is carried out at a temperature of about 200° to about 400° C. and a pressure of about 200 to about 2000 psi.

9. A process according to claim 2 wherein the process is carried out in the presence of hydrogen.

10. A process according to claim 1 wherein the ratio of secondary alcohol to HOMeTHF or FTHF is about 1:1 to about 500:1, and the catalyst is present at a level to provide a gram atom Zr to mole of HOMeTHF or FTHF ratio of about 0.01:1 to about 0.5:1.

11. A process for preparing MeTHF, which comprises contacting HOMeTHF or FTHF in a reaction zone with a secondary alcohol selected from the group consisting of 2-propanol and cyclohexanol, in the presence of a catalyst consisting essentially of hydrous zirconia under an inert atmosphere.

12. A process according to claim 11 wherein the secondary alcohol is 2-propanol and the inert atmosphere comprises nitrogen or carbon dioxide.

13. A process according to claim 12 wherein the contacting is carried out in the presence of a solvent selected from the group consisting of water, tetrahydrofuran, tetrahydropyran, toluene, xylenes, and alkanes of 5 to 20 carbons.

14. A process according to claim 12 wherein the process is carried out in the presence of hydrogen.

15. A process according to claim 12 wherein the ratio of secondary alcohol to HOMeTHF or FTHF is about 5:1 to about 100:1, and the catalyst is present at a level to provide a gram atom Zr to mole of HOMeTHF or FTHF ratio of about 0.1:1 to about 2:1.

16. A process for preparing MeTHF, which comprises contacting HOMeTHF or FTHF in a reaction zone with water and a secondary alcohol selected from the group consisting of 2-propanol and cyclohexanol, in the presence of a catalyst consisting essentially of hydrous zirconia under an atmosphere comprising nitrogen or carbon dioxide, wherein the process is performed at a temperature of about 260° to about 350° C. and at a pressure of about 400 to about 800 psi.

17. A process according to claim 16 wherein the process is carried out in the presence of hydrogen.

* * * * *

UNITED STATES PATENT AND TRADEMARK OFFICE
CERTIFICATE OF CORRECTION

PATENT NO. : 6,812,354 B2
DATED : November 2, 2004
INVENTOR(S) : Beavers et al.

It is certified that error appears in the above-identified patent and that said Letters Patent is hereby corrected as shown below:

<u>Title page,</u>
Item [73], "Assignee: Eastman Kodak Company, Kingsport, TN (US)" should read
-- Assignee: Eastman Chemical Company, Kingsport, TN (US) --.

Signed and Sealed this

First Day of March, 2005

JON W. DUDAS
*Director of the United States Patent and Trademark Office*